(12) United States Patent
Mizuno et al.

(10) Patent No.: US 7,848,625 B2
(45) Date of Patent: Dec. 7, 2010

(54) IMAGING SYSTEM

(75) Inventors: Takashi Mizuno, Hamamatsu (JP);
Takayoshi Suzuki, Hamamatsu (JP);
Yutaka Mizukusa, Chofu (JP)

(73) Assignee: Kowa Company Ltd. (JP)

( * ) Notice: Subject to any disclaimer, the term of this patent is extended or adjusted under 35 U.S.C. 154(b) by 516 days.

(21) Appl. No.: 11/655,567

(22) Filed: Jan. 19, 2007

(65) Prior Publication Data

US 2007/0183760 A1      Aug. 9, 2007

(30) Foreign Application Priority Data

Feb. 8, 2006      (JP)      ............... 2006-030701

(51) Int. Cl.
*G03B 29/00*      (2006.01)
*A61B 3/14*      (2006.01)
(52) U.S. Cl. ..................... 396/18; 351/206; 348/78
(58) Field of Classification Search ............... 396/18; 351/206, 207; 348/78
See application file for complete search history.

(56) References Cited

U.S. PATENT DOCUMENTS 5,713,047 A * 1/1998 Kohayakawa ............... 396/18

FOREIGN PATENT DOCUMENTS

EP      1797816 A2      6/2007
JP      2005-312764 A      11/2005

OTHER PUBLICATIONS

Translation of JP 2005-312764 A.*
A Communication pursuant to Article 94(3) of the European Office Action dated Jan. 26, 2009 issued in related European Patent Application No. 07 001 798.3-1265.

* cited by examiner

*Primary Examiner*—Rochelle-Ann J Blackman
(74) *Attorney, Agent, or Firm*—Adams & Wilks

(57) ABSTRACT

An imaging system is provided that is capable of controlling a photographic operation to provide favorable images of a fundus of an eye to be examined. When a normal photographic mode is selected, a single operation of a shutter button causes a single trigger signal to be generated. On the other hand, when a stereo photographic mode is selected, a single operation of a shutter button causes two trigger signals to be generated in succession. The generated trigger signal triggers a switching device so that a position of a photographic stop is automatically switched to a position predetermined for the photographic mode, and the photographic light source is caused to emit light a number of times that corresponds to the selected photographic mode. In such a configuration, fundus images are automatically produced a set number of times by a single operation of the shutter. Therefore, a high-quality fundus image can be obtained without concerns that an appropriate moment to capture an image will be missed.

16 Claims, 18 Drawing Sheets

PRIOR ART

S1     TRIGGER SIGNAL
S2     STROBE SIGNAL
S11    TRIGGER MASK SIGNAL
S12    STROBE MASK SIGNAL

PRIOR ART

IMAGING SYSTEM

BACKGROUND OF THE INVENTION

1. Field of the Invention

The present invention relates to an imaging system, and in particular relates to an imaging system comprising a photographic apparatus for causing a photographic light source to emit light momentarily via the operation of a shutter button to photograph a fundus of an eye to be examined a preset number of times.

2. Description of the Prior Art

One type of ophthalmologic examination that has conventionally been performed involves strobe light being emitted, whereby a fundus is imaged using a fundus camera comprising a CCD or other imaging device, and the resulting fundus image is captured as an image signal in a computer or another image capturing device.

FIG. 18a shows an example of such an imaging system. In a fundus camera 100, a trigger signal generating button is pressed, whereby a trigger signal S1 is generated, and, based on the trigger signal, an image capturing device 101 generates a strobe signal S2 for the fundus camera 100 and an imaging device 102. On receiving the strobe signal S2, the fundus camera 100 generates strobe light and drives an internal optical component, and the imaging device 102 produces an image obtained from the optical system of the fundus camera. The image produced in the imaging device 102 is captured as an image signal in the image capturing device 101, and is then processed, recorded, and saved as required.

Meanwhile, once the trigger signal has been generated, the fundus camera 100 generates a trigger mask signal S11 for keeping the trigger signal from being generated for a fixed period of time, and a strobe mask signal S12 for keeping the emission of strobe light or another photographic operation prompted by the strobe signal from being performed multiple times, and these signals are employed in the above-described operation. A method also exists wherein a strobe-enabling signal rather than the strobe mask signal is generated and employed.

In an example of a conventional system shown in FIG. 18a, the image capturing device 101 or another external device is invariably necessary. However, in the example of a system shown in FIG. 18b, an external device is not strictly necessary, the fundus camera 100 generates a trigger signal S1 to the imaging device 102, and the imaging device 102 generates a strobe signal S2 to the fundus camera 100 simultaneously on receipt of the signal S1 or when otherwise suitable for image capture. On receiving the strobe signal S2, the fundus camera 100 then generates strobe light or performs another action in the same manner as in the example of the system shown in FIG. 18a. In FIG. 18b, the imaging device 102 and image capturing device 101 are shown in a connected state. However, the image capturing device 101 is not strictly necessary when a memory device is incorporated in the imaging device 102.

Traditionally, stereophotography is used to provide two images having a parallax from the same fundus, and these images are displayed as a pair, whereby the fundus can be viewed stereoscopically. A fundus camera able to capture such stereo images having a parallax is provided with a photographic stop in which right and left apertures are formed (two-aperture stop). In accordance with the shutter operation, an image is captured from one aperture of the photographic stop and then from the other aperture, strobe light is generated for each, and two images for stereoscopic viewing are obtained in succession (see Japanese Laid-open patent application 1984-90547)

In a conventional system, the capturing of two stereo images having parallax necessarily involves operating a trigger signal generating button (or the like) at least twice, and causing the strobes to be emitted in succession. A problem arises in that an opportunity to obtain a favorable stereo image will be lost due to slow operation of the shutter.

It is therefore an object of the invention to provide an imaging system being capable of controlling a photographic operation in which a light source is caused to emit light a preset number of times and capable of providing a favorable image for each photography.

SUMMARY OF THE INVENTION

An imaging system according to the present invention comprises a photographic apparatus capable of controlling a photographic operation in which a shutter button is operated to cause a photographic light source to momentarily emit light to photograph an object. The system comprises means for selecting a photographic mode; and means for controlling the photographic operation such that, when a first photographic mode is selected, a single operation of the shutter button causes a single photographic operation to be performed, and, when a second photographic mode is selected, a single operation of the shutter button causes a plurality of photographic operations to be successively performed, wherein, for each of the photographic operations, photographic conditions are set to those that are predetermined for the photographic operation.

The system also comprises means for selecting a photographic mode; and means for controlling the photographic operation such that, when a first photographic mode is selected, a single operation of the shutter button causes the photographic light source to emit light for still image photography, and, when a second photographic mode is selected, a single operation of the shutter button causes the object to be photographed as an moving image for a predetermined period of time, the photographic light source being caused to emit light a plurality of times during said period of time.

In addition, the system comprises means for selecting a photographic mode; and means for controlling the photographic operation such that, when a first photographic mode is selected, a single operation of the shutter button causes a single photographic operation to be performed, and, when a second photographic mode is selected, a single operation of the shutter button causes a plurality of photographic operations to be successively performed, wherein at least the position of a photographic stop is set to a position that is preset for each of the photographic operations.

In the invention, a single operation of the shutter button causes the photographic light source to emit light the number of times that is determined in accordance with the photographic mode. To take photographs, the photographic conditions such as the photographic stop position and the like are automatically set to those that are predetermined for each photography. This assures that a high-quality image can be captured without concerns that the appropriate moment to capture the image will be missed.

Further features of the invention, its nature and various advantages will be more apparent from the accompanying drawings and following detailed description of the invention.

BRIEF DESCRIPTION OF THE DRAWINGS

FIG. 17b is a timing diagram showing points at which the signals are generated in the configuration of FIG. 17a.

DESCRIPTION OF THE PREFERRED EMBODIMENTS

The present invention will be described in detail hereunder with reference to the attached drawings using as an example an imaging system comprising a photographic apparatus (fundus camera) for photographing a fundus of an eye to be examined as an object.

Figure 1:
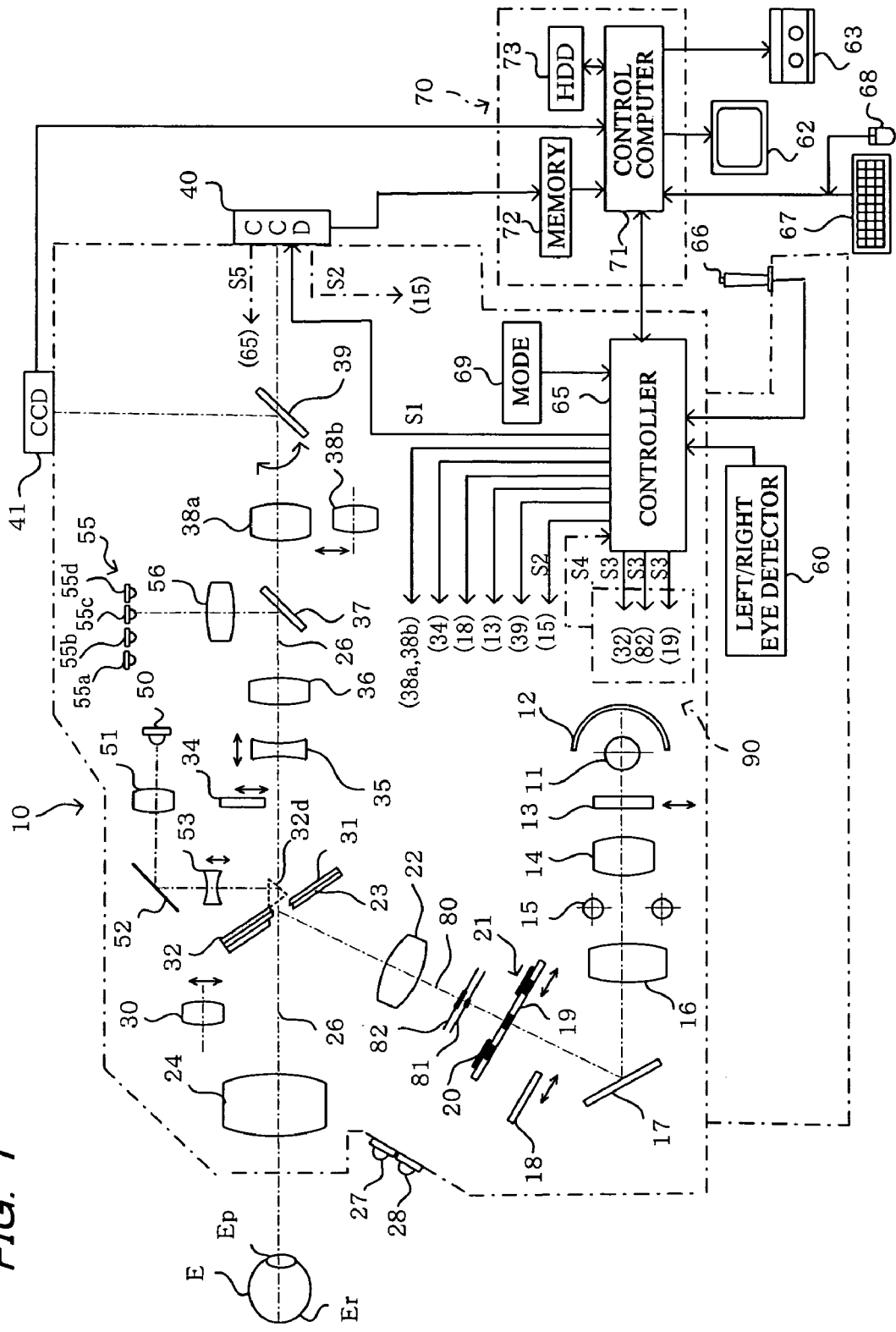
FIG. 1 is a block diagram showing a configuration of an imaging system of the present invention.

As shown in FIG. 1, an imaging system according to the present embodiment comprises a fundus camera unit (main unit) 10, a CCD or another imaging device 40 for producing a fundus image as an electronic image, an image capturing device 70 composed of a computer or another device for capturing the fundus image, display devices 62 and 63, input devices 67 and 68, and the like.

In the fundus camera unit 10, an observation lamp 11 for emitting infrared and visible illumination light is disposed in the center of curvature of a spherical mirror 12. Light from the observation lamp 11 and spherical mirror 12 passes through a visible light cutting/infrared light transmitting filter 13 that can be inserted into and removed from the optical path, a condenser lens 14, a strobe unit 15 for use as a photographic light source, and a condenser lens 16, and then impinges on a total reflection mirror 17.

Illumination light reflected by the total reflection mirror 17 is transmitted through a ring slit 21 as an illumination stop, a black spot plate 81 for use in normal image capture, a black spot plate 82 for use in stereoscopic image capture and a relay lens 22, is reflected by an apertured total reflection mirror 23 and is made incident on an anterior ocular segment (pupil) Ep of an eye to be examined E via an objective lens 24.

Figure 5A:
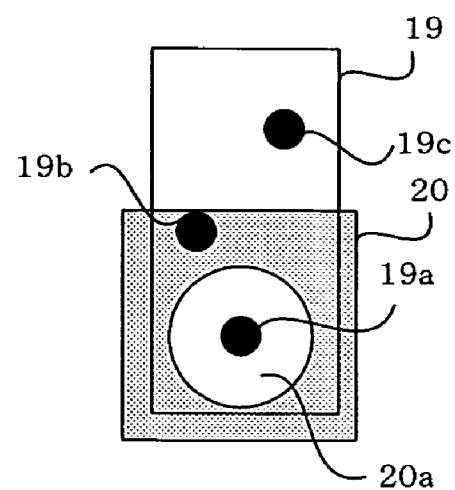
FIGS. 5a through 5c are illustrative views each showing a manner in which an illumination stop is switched.
Figure 5B:
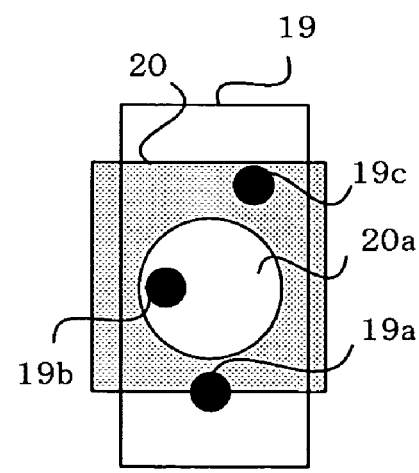
Figure 5C:
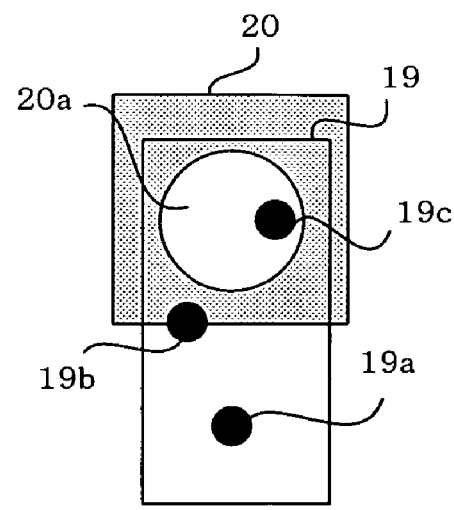

The ring slit 21 is composed of a movable stop 19 and a fixed stop 20, and is disposed in the illuminating optical system at a position substantially conjugate with the anterior ocular segment Ep (pupil) of the eye to be examined. As shown in FIGS. 5a through 5c, the movable stop 19 is composed of a transparent glass plate having circular light shields 19a, 19b and 19c. The fixed stop 20 is an opened stop having an opening 20a at the center, and the movable stop 19 is positioned as shown in FIGS. 5a, 5b and 5c in accordance with the movement thereof. The illumination stop is switched to a stop having an illumination light pattern that corresponds to the position of the movable stop 19.

Reflected light from the fundus Er illuminated by the illuminating optical system passes through a photographic optical system having the objective lens 24, the apertured total reflection mirror 23, a fixed stop 31, a movable stop unit 32, a focusing lens 35, an imaging lens 36, a half mirror 37 and a variable power lens 38a, and impinges on a return mirror 39. At the position where the return mirror 39 is shown in the drawings, reflected light from the fundus impinges on an infrared-light sensitive CCD (imaging device) 41 positioned conjugate with the fundus, and the fundus is imaged by the CCD 41. If the return mirror 39 is removed from the optical path, reflected light from the fundus will impinge on a visible-light sensitive CCD (imaging device) 40 positioned conjugate with the fundus, and an image of the fundus will be produced by the CCD 40.

Figure 2A:
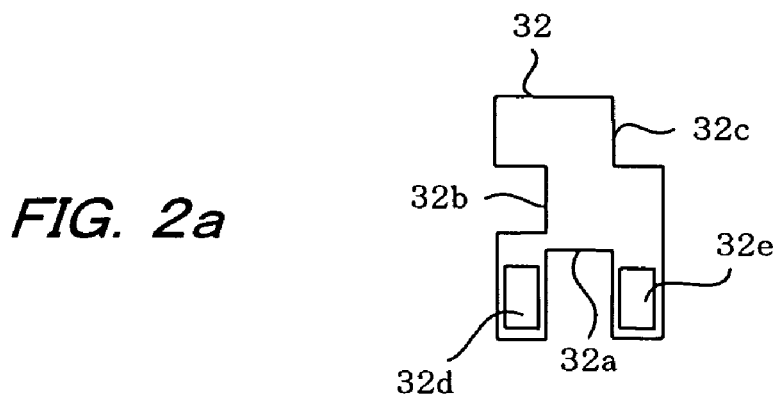
FIG. 2a is a plan view showing a configuration of a movable stop unit.
Figure 2B:
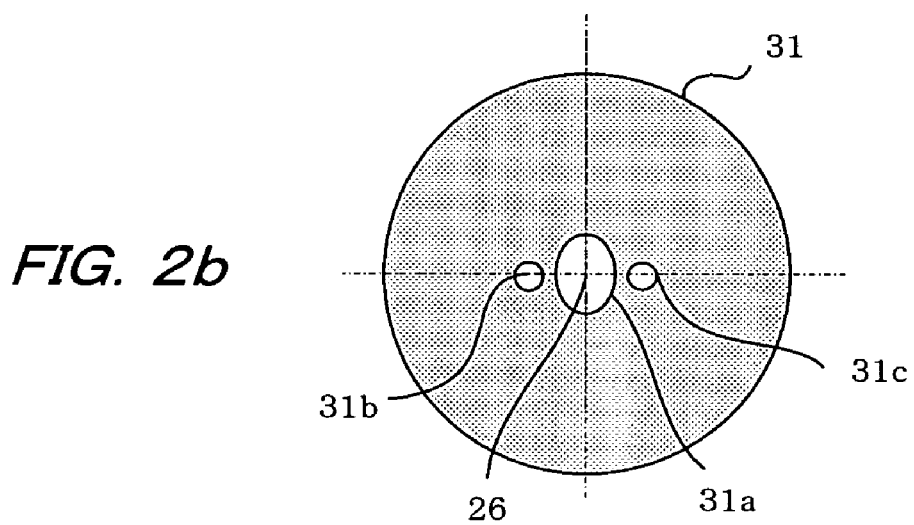
FIG. 2b is a plan view showing a configuration of a fixed stop.
Figure 2C:
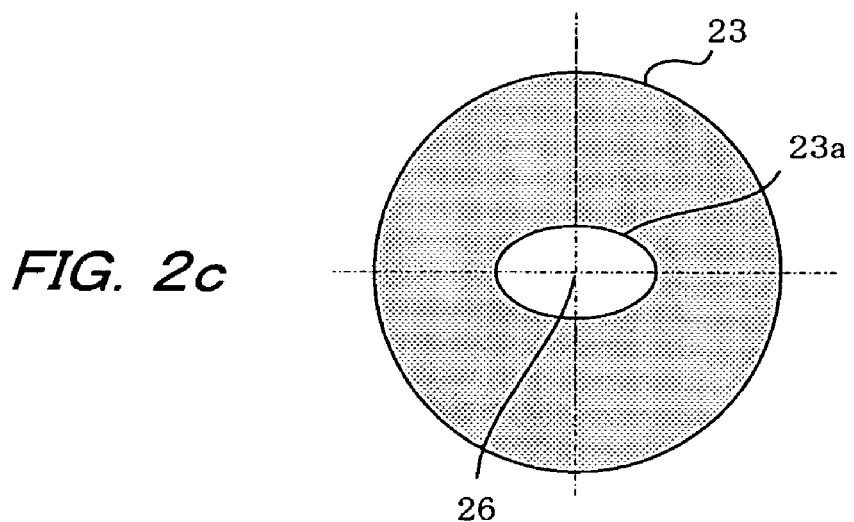
FIG. 2c is a plan view showing a configuration of an apertured total reflection mirror.

The apertured total reflection mirror 23 is a total reflection mirror provided at its central part with an opening 23a, as shown in FIG. 2c. As shown in FIG. 2b, the fixed stop 31 is a stop provided at its central part with a photographic stop 31a for use in normal image capture and provided on either side of the photographic stop 31a with photographic stops (two-aperture stops) 31b and 31c for projecting a focus marker and obtaining stereo images. The fixed stop 31 is tightly attached and fixed to the apertured total reflection mirror 23.

The photographic stops 31a, 31b, 31c are disposed in positions substantially conjugate with the anterior ocular segment (pupil) of the eye to be examined. The center of the photographic stop 31a is disposed in a position (first position) that is coaxial with an optical axis (optical axis of the photographic optical system) 26 of the objective lens 24. The photographic optical path is laterally divided at a position conjugate to the pupil in order to obtain left and right images for stereoscopic viewing. The photographic stops 31b and 31c are disposed on the left optical path position (second position) and right optical path position (third position), respectively.

Figure 3A:
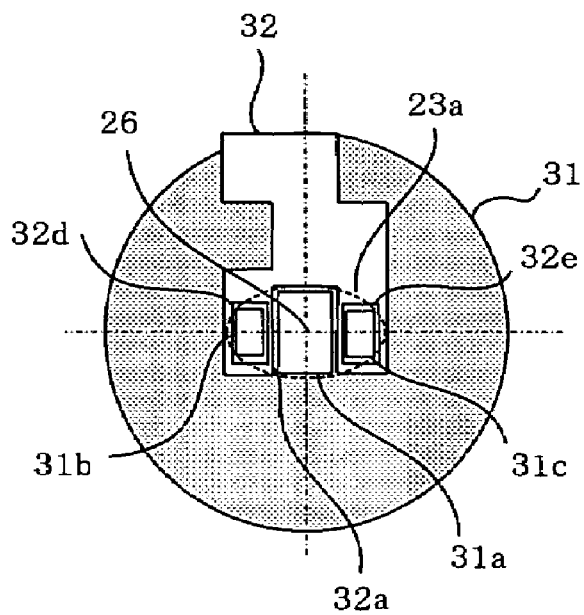
FIGS. 3a through 3c are illustrative views each showing a state in which a photographic aperture is selected according to a movement of the movable stop unit.
Figure 3B:
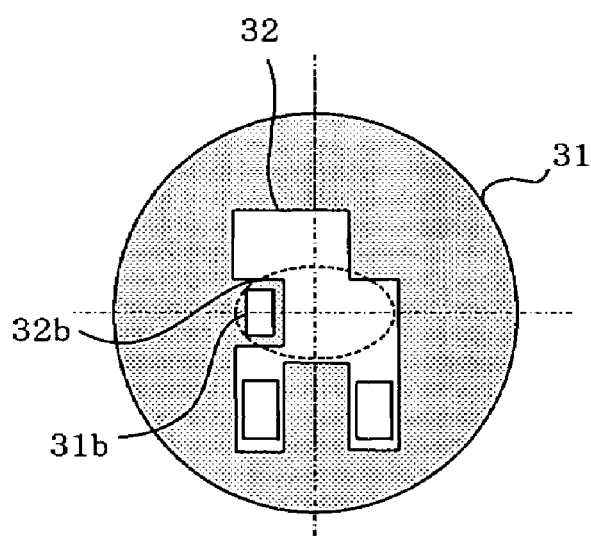
Figure 3C:
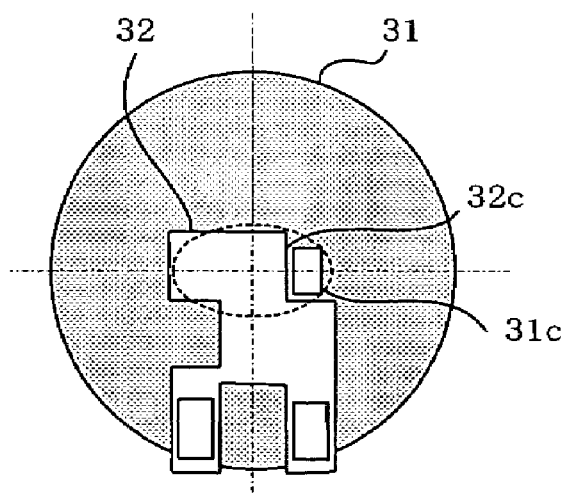
Figure 4:
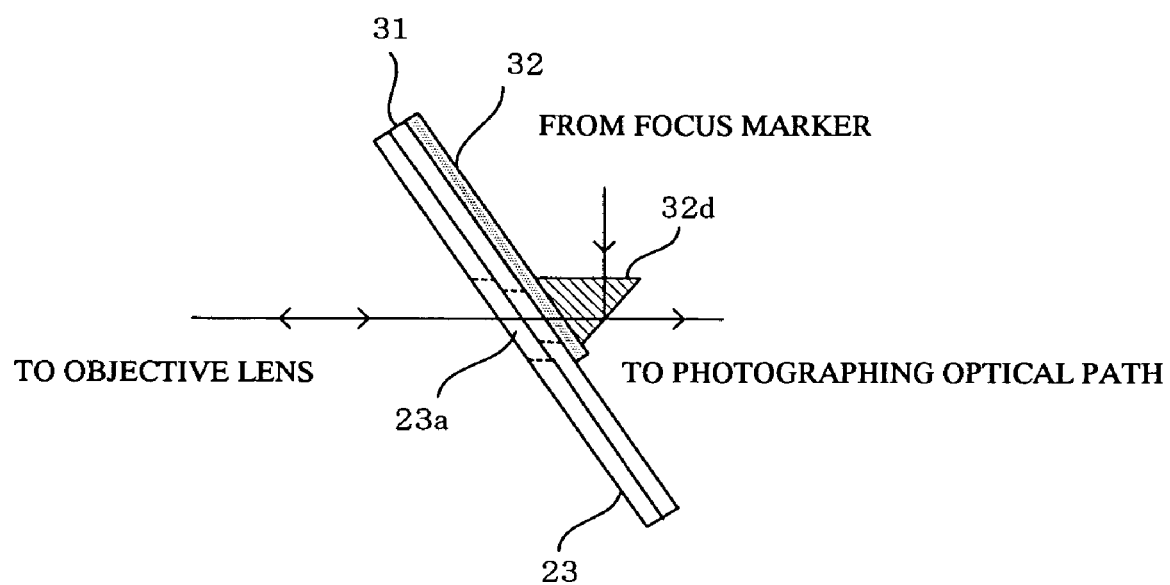
FIG. 4 is an illustrative view showing in detail a path of a light beam that travels through a photographic stop.

As shown in FIG. 2a, the movable stop unit 32 has cutout parts 32a, 32b and 32c. Reflecting prisms 32d and 32e (refer also to FIG. 4) for reflecting a focus marker toward the fundus are provided to either side of the cutout part 32a. When the movable stop unit 32 moves vertically to the position shown in FIG. 3a, the cutout part 32a opens the opening of the photographic stop 31a. This causes the photographic stop 31a to be selected and the photographic stop to be switched to the photographic stop 31a. When the movable stop unit 32 moves to the positions shown in FIGS. 3b and 3c, the cutout parts 32b and 32c open the photographic stops 31b and 31c, respectively. This causes the photographic stop 31b or 31c to be selected and the photographic stop to be switched to the photographic stop 31b or 31c.

Figure 6A:
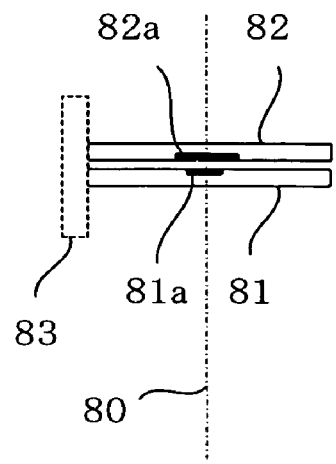
FIGS. 6a and 6b are illustrative views each showing a state in which a black spot is changed in accordance with a photographic mode.
Figure 6B:
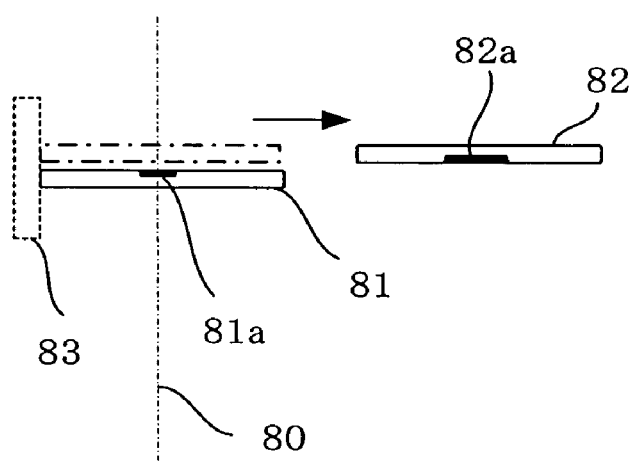

The black spot plate 81 for use in normal photography has a circular black spot 81a in the center, as shown in FIGS. 6a and 6b. The black spot plate 82 for use in stereoscopic photography has a circular black spot 82a in the center. The black spots 81a and 82a are each disposed at positions substantially conjugate with the photographic stop in relation to the image of reflected photographic light by the objective lens 24. As described above, when stereo image mode has been selected, the black spot plates 81 and 82 both come into contact with a stopper 83, as shown in FIG. 6a. The centers of the black spots 81a and 82a reach a position that is coaxial with an optical axis 80 of the illuminating optical system. This enables the black spot 82a. On the other hand, in normal image mode, the black spot plate 82 is removed from the optical path of the illuminating optical system, thereby enabling the black spot 81a. In either mode, reflected light generated by photographic light that reflects on the surface of the objective lens 24 is prevented from entering the photographic stop.

Returning to FIG. 1, an anterior ocular segment lens 30 is removably disposed in the optical path between the objective lens 24 and the apertured total reflection mirror 23. An infrared light source 27 for illuminating the anterior ocular segment Ep with infrared light is provided in order to perform alignment using the anterior ocular segment, and a light source 28 for illuminating the anterior ocular segment with weak white light is provided in order to photograph the anterior ocular segment.

An optical system for projecting a focus marker is also provided to the fundus camera. In the projecting optical system, marker light from a focus marker light source 50 composed of an infrared LED is transmitted through a lens 51, a mirror 52, and a lens 53, and is projected onto the fundus Er, with the optical path divided in two by reflecting prisms 32d and 32e fixed to the movable stop unit 32. When the focusing lens 35 is moved in order to adjust the focus, the position of the lens 53 moves correspondingly, and the separated images of the focus marker changes on the fundus Er. The examiner therefore moves the focusing lens 35 so that the images of the marker come into alignment. This brings the fundus into focus.

An exciter filter 18 is inserted into the optical path of the illuminating optical system during fluorescence photography, and a barrier filter 34 is inserted on the examined eye side of the focusing lens 35 during fluorescence photography. An internal fixation lamp 55 composed of a plurality of fixation lamps 55a to 55d is provided in order to cause the eye being examined to fixate toward the fundus camera.

The fundus imaged by the CCD 41, or the image of the anterior ocular segment is input to an image capturing device 70, and is processed by a control computer 71 composed of a CPU or other device, and the captured image are displayed as a moving image on a monitor 62. A stereo monitor 63 is additionally provided as a display specifically for stereoscopic viewing. The examiner can stereoscopically view the fundus via the stereo monitor 63 by observing the stereoscopically captured right and left images.

The CCD 40 images the fundus illuminated by the strobe unit 15 as a still image when a shutter button 66 provided to a joystick is operated. The fundus image is temporarily stored in high-speed memory 72 in the image capturing device 70, is transferred by the control computer 71 at a preset timing to a low-speed hard disk (recording device) 73 used as an external recording device, and is then either recorded or displayed on the monitor 62 or stereo monitor 63.

A keyboard 67, mouse 68, or other input means is additionally provided. A variety of data can be input via these input means.

A controller (control means) 65 composed of a CPU or another device is further provided to the fundus camera. The controller 65 is connected to the control computer 71 of the image capturing device 70 and is allowed to exchange signals therewith, while also outputting a trigger signal S1 to the CCD 40 when the shutter button 66 is operated. A strobe signal S2 for causing the strobe unit 15 to momentarily emit light is generated by the controller 65 or the CCD 40. The controller 65 also controls the operations whereby the following components are inserted into and removed from the optical path: the return mirror 39, visible light cutting/infrared light transmitting filter 13, exciter filter 18, barrier filter 34, anterior ocular segment lens 30, and variable power lenses 38a and 38b.

Photographic mode selection means 69 for selecting normal, stereo, or another photographic mode is also provided to the fundus camera, and a signal indicating the selected mode is input to the controller 65. The controller 65 generates a movement command signal S3 in accordance with the selected mode, moves the movable stop unit 32 and switches the photographic stop, moves the movable stop 19 to switch the illumination stop, and moves the black spot plate 82 to switch the black spot. The movable stop unit 32, movable stop 19, and black spot plate 82 are moved by associated actuators (not shown). The actuators are collectively designated as a switching device 90 and are shown in the drawings as a block having an imaginary line.

A left/right eye detector 60 for detecting whether the eye to be examined is a left eye or a right eye is further provided to the fundus camera. Detected information regarding whether the eye is a left eye or a right eye is input to the controller 65.

In such a configuration, anterior ocular segment alignment is performed while the image of the anterior ocular segment created by the CCD 41 is observed using the monitor 62. Once alignment is complete, the anterior ocular segment lens 30 is removed from the optical path, and light from the fundus is transmitted through the aperture 23a in the apertured total reflection mirror 23 and through the photographic stop 31a. The CCD 41 produces the fundus image, which is then displayed on the monitor 62. The examiner therefore performs alignment by observing the fundus image, and operates the focus lens 35 to adjust the focus.

When fundus alignment and focus adjustment are complete, the shutter button 66 is operated. The photographic operation starts when the shutter button 66 is operated. FIGS. 7 through 12 show a variety of examples of the flow of signals from individual components and the timing at which those signals are generated during the photographic operation.

Figure 7A:
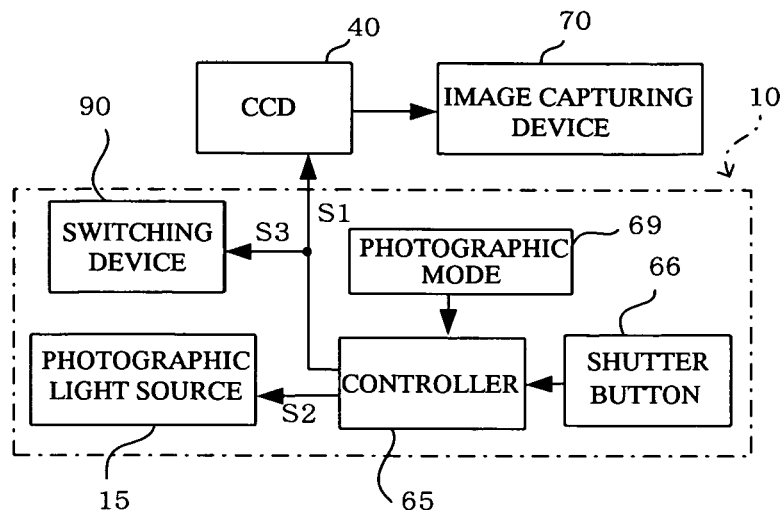
FIG. 7a is a block diagram showing an example of a system for generating a trigger signal a preset number of times and capturing images by a single operation of a shutter button.
Figure 7B:
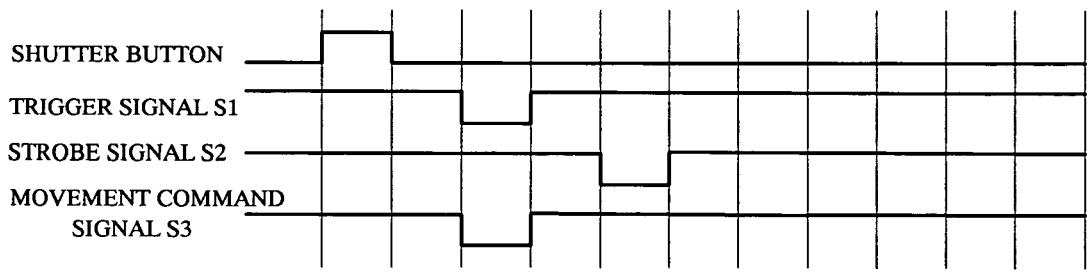
FIGS. 7b and 7c are timing diagrams showing the timing at which the signals are generated.
Figure 7C:
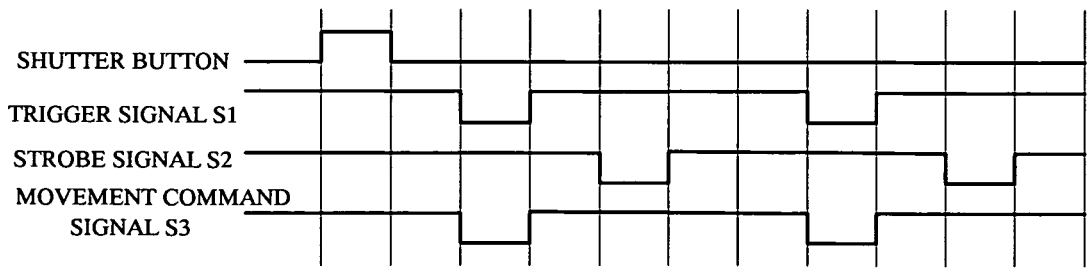

In the example shown in FIGS. 7a through 7c, the trigger signal S1 is output to the CCD 40 once or a plurality of times in accordance with the photographic mode by the operation of the shutter button 66, and a movement command signal S3 is output to the switching device 90 synchronously with the trigger signal S1. FIG. 7a schematically shows the components of FIG. 1 as blocks in order to make the flow of the signals more readily understood. FIG. 7b is a diagram of the signal timing in the normal mode in which normal (monocular) photographing is performed to photograph the fundus as a single image. FIG. 7c is a diagram of the signal timing in a photographic mode when stereophotography is performed to photograph the fundus as a right/left pair of images having a parallax.

When the normal photographic mode has been selected by the photographic mode selection means 69 and the shutter button 66 is depressed, the controller 65 outputs a trigger signal S1 to the CCD 40, and a movement command signal S3 is output to the switching device 90 synchronously with the trigger signal S1. The switching device 90 receives the movement command signal S3, moves the movable stop unit 32 to the position shown in FIG. 3a and switches to the photographic stop 31a, moves the movable stop 19 to the position shown in FIG. 5a and switches to the illumination stop. This causes the light shield 19a to be positioned in the center of the opening 20a of the fixed stop 20. The switching device 90, as shown in FIG. 6b, also removes the black spot plate 82 from the optical path and switches to the black spot 81a. The return mirror 39 is also removed from the optical path synchronously with the movement command signal S3. The controller 65 then outputs a strobe signal S2 to the strobe unit 15, and the strobe unit 15 emits light. An image of the fundus illuminated by the strobe light is produced by the CCD 40, and an image signal thereof is captured by the image capturing device 70.

On the other hand, when the stereo mode for capturing stereo images (stereoscopic photography) is set, a trigger signal S1 is automatically output from the controller 65 a plurality of times (two times) by a single operation of the shutter button 66. A movement command signal S3 is output to the switching device 90 synchronously with the outputting of the first trigger signal S1 to the CCD 40. The switching device 90 receives the movement command signal S3, moves the movable stop unit 32 to the position shown in FIG. 3b and switches to the photographic stop 31b. The switching device 90 further moves the movable stop 19 to the position shown in FIG. 5b and switches to the illumination stop with the light shield 19b being positioned in the opening 20a of the fixed stop 20. The black spot also moves into the position shown in FIG. 6a to enable the black spot 82b for stereophotography. In addition, the return mirror 39 is removed from the optical path synchronously with the movement command signal S3. Next, the controller 65 outputs a strobe signal S2 to the strobe unit 15 to cause the strobe unit 15 to emit light. This enables one fundus image with a parallax for stereoscopic viewing to be created by the CCD 40, and an associated image signal is captured by the image capturing device 70.

A second trigger signal S1 is generated by the controller 65, and a movement command signal S3 is generated synchronously with the trigger signal S1. The movable stop unit 32 is moved to the position shown in FIG. 3c, the movable stop 19 is moved to the position shown in FIG. 5c, and these two members are switched, respectively, to the photographic stop 31c and the illumination stop with the light shield 19c being positioned in the opening 20a of the fixed stop 20. Next, the strobe unit 15 emits light in accordance with a strobe signal S2 from the controller 65. This causes the other fundus image with a parallax for stereoscopic viewing to be created by the CCD 40, and an associated image signal is captured by the image capturing device 70.

Thus, when normal or stereo photography is performed, the controller 65 controls the photographic operations with the photographic conditions such as the position of the photographic stop, the position of the illumination stop, the position of the black spot and the like being set for each of the photographic operations to those that are predetermined for the photographic operation.

Figure 8A:
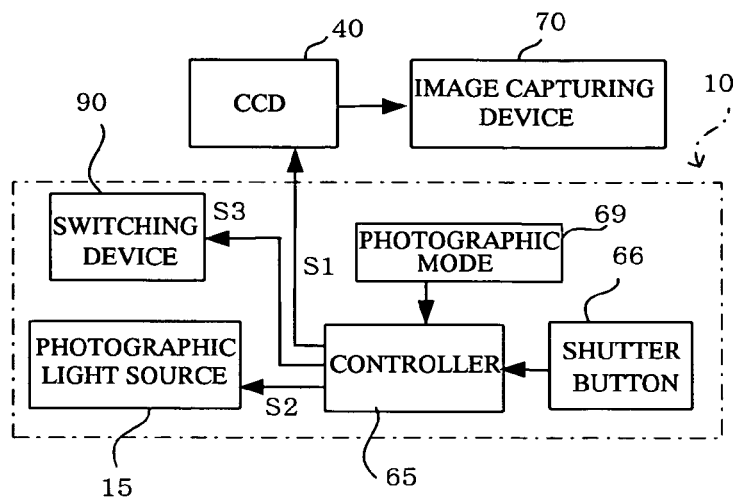
FIG. 8a is a block diagram showing an example of a system for generating a trigger signal a preset number of times and capturing images by a single operation of a shutter button.
Figure 8B:
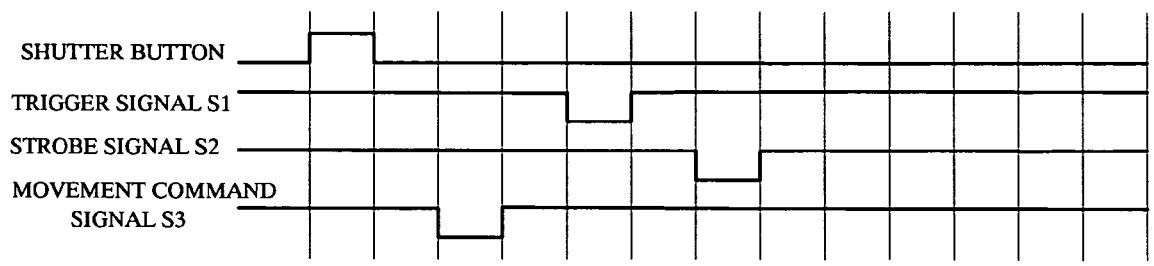
FIGS. 8b and 8c are timing diagrams showing the timing at which the signals are generated.
Figure 8C:
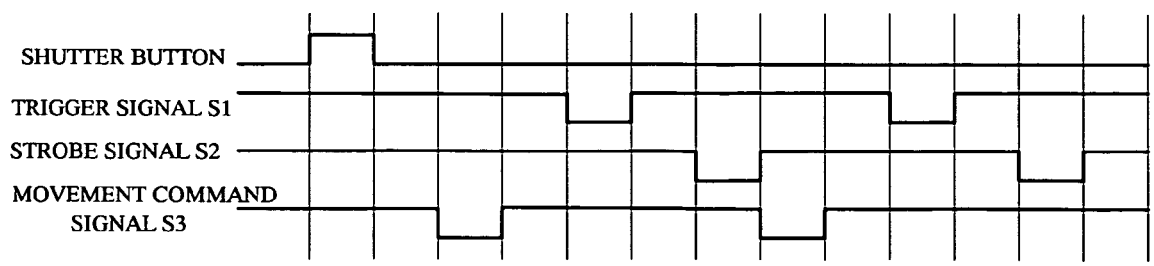

In the example shown in FIGS. 8a through 8c, the trigger signal S1 and the movement command signal S3 produced from the controller 65 are generated asynchronously. Therefore, the point at which the movement command signal S3 is generated is a certain period of time before the point at which the trigger signal S1 is generated.

Figure 9A:
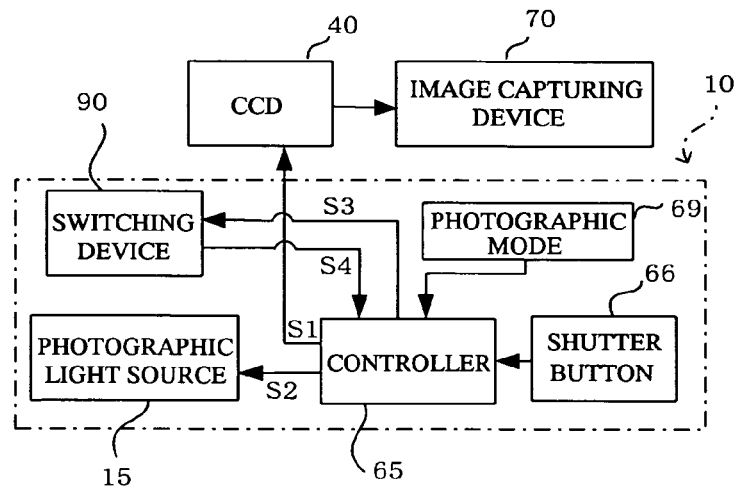
FIG. 9a is a block diagram showing another example of a system for generating a trigger signal a preset number of times and capturing images by a single operation of a shutter button.
Figure 9B:
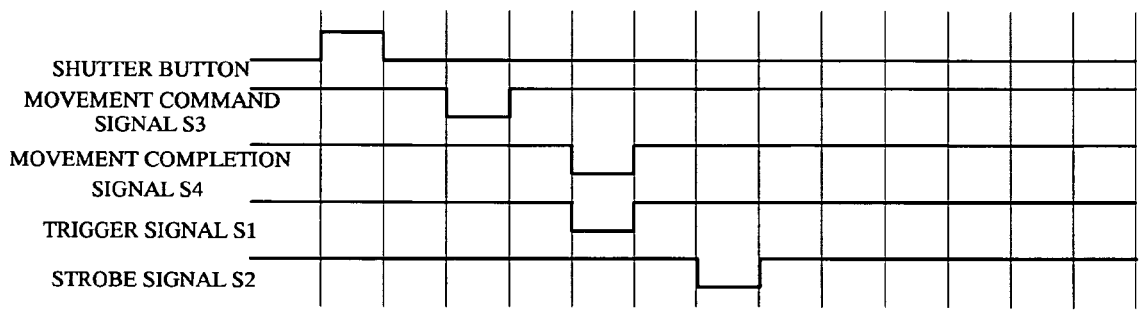
FIGS. 9b and 9c are timing diagrams showing the timing at which the signals are generated.
Figure 9C:
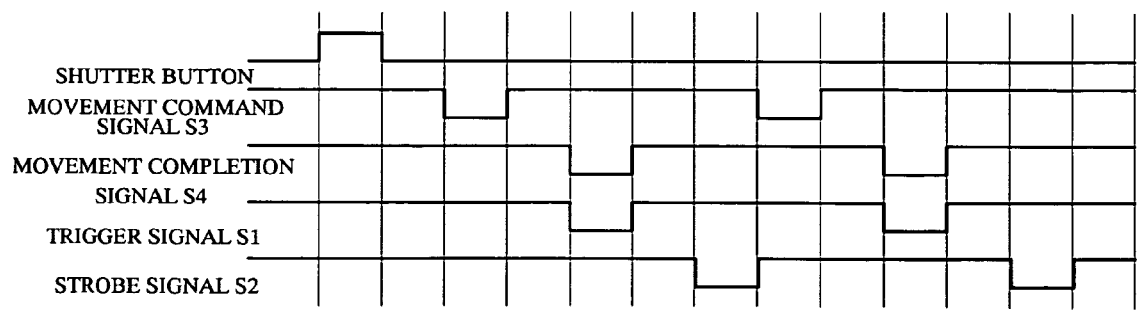

In the example shown in FIGS. 9a through 9c, once the shutter button 66 has been operated, the controller 65 outputs a movement command signal S3 to move the movable members (32, 19, 82) to positions suitable for each photography and set the photographic conditions to those suitable for photographing. Next, a trigger signal S1 is output from the controller 65 synchronously with the reception of the movement completion signal S4 of the moving members from the switching device 90. For example, the following means are considered for detecting the completion of the movement of the movable members.

When a reflective sensor is used, a reflective surface (or non-reflective surface) is provided to part of the movable stop unit 32, movable stop 19, and black spot plate 82, and the reflective surface is detected. When a transmission-type sensor is used, the movable stop unit 32, movable stop 19, and black spot plate 82 are modified to such an arrangement (configuration) that the sensor is blocked (or made transmissive) when the movable members each move to a preset position. When a microswitch is employed, the movable stop unit 32, movable stop 19, and black spot plate 82 are disposed so that the switch is turned on when the movable members themselves (or the driving parts of the actuators) reach preset positions. When a stepping motor is used as the actuator, the completion of the movement is detected in accordance with the number of steps.

Figure 10A:
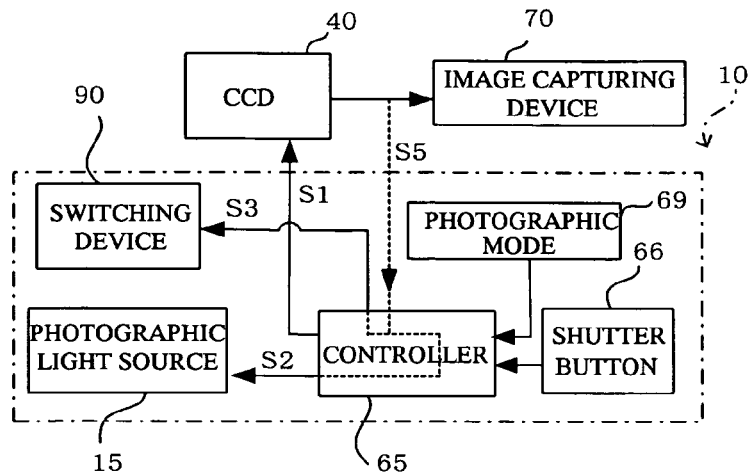
FIG. 10a is a block diagram showing still another example of a system for generating a trigger signal a preset number of times and capturing images by a single operation of a shutter button.
Figure 10B:
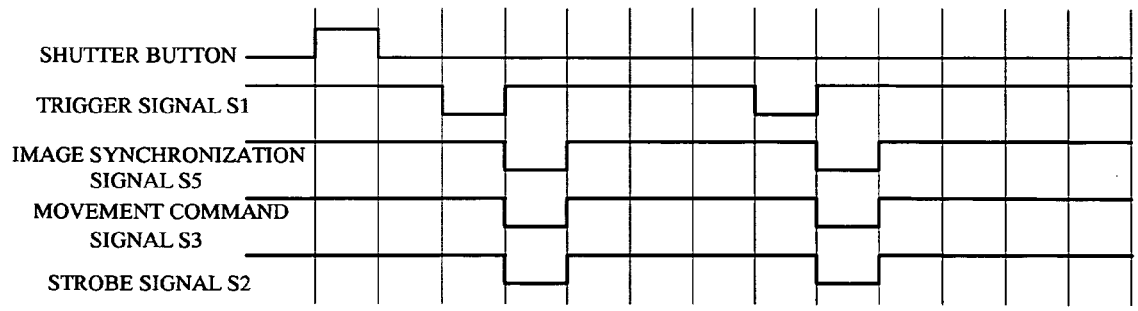
FIGS. 10b and 10c are timing diagrams showing the timing at which the signals are generated.
Figure 10C:
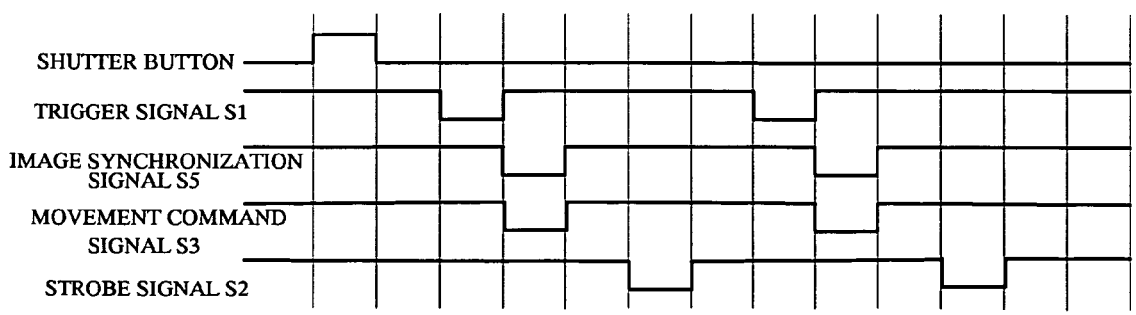

In the example shown in FIGS. 10a through 10c, an image synchronization signal (vertical synchronization signal) S5 from the CCD 40 is used for the strobe signal S2 and movement command signal S3. When a trigger signal S1 is output to the CCD 40 by operating the shutter button 66, the image synchronization signal S5 output from the CCD 40 is input to the controller 65. A movement command signal S3 and strobe signal S2 are then generated synchronously with the image synchronization signal S5. This causes the movable members (32, 19, 82) to be moved to positions suitable for photography and the strobe unit 15 to emit light to perform photographing (see the timing chart of FIG. 10b). To cause the strobe to emit light after completion of the movement of the movable members, the strobe signal S2 may also be generated after a certain period of time once the movement command signal S3 synchronized with the image synchronization signal has been generated, as shown in the timing chart of FIG. 10c.

Figure 11A:
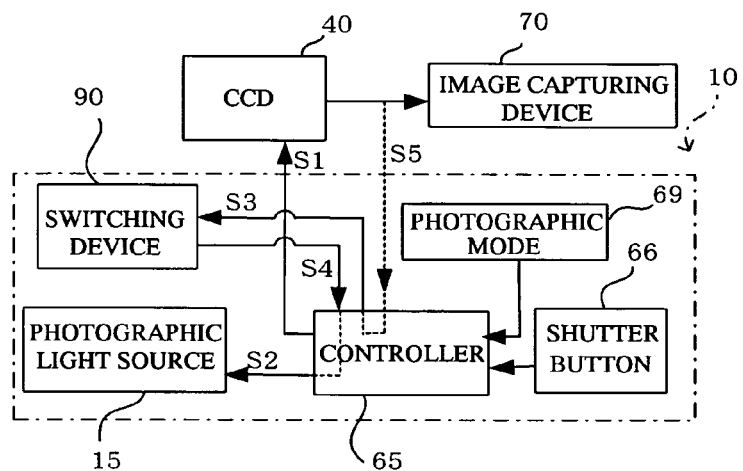
FIG. 11a is a block diagram showing yet another example of a system for generating a trigger signal a preset number of times and capturing images by a single operation of a shutter button.
Figure 11B:
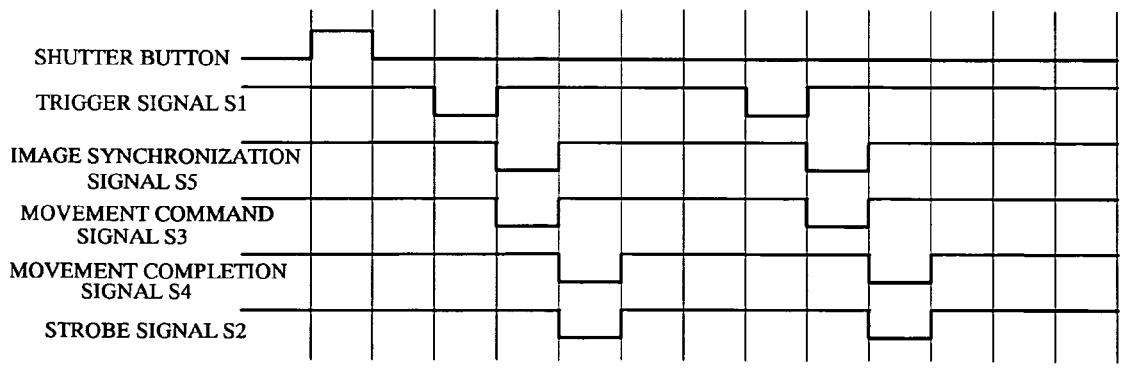
FIG. 11b is a timing diagram showing the timing at which the signals are generated.

In the example shown in FIGS. 11a and 11b, the controller 65 sends a trigger signal S1 to the CCD 40 in response to the operation of the shutter button 66. The controller 65 then generates a movement command signal S3 synchronously with an image synchronization signal S5 generated by the CCD 40 and moves the movable members. The switching device 90 switches to the photographic stop, illumination stop, and black spot disposed at positions suitable for photography. The controller 65 generates a strobe signal S2 upon receiving a signal S4 from the switching device 90 indicating that the movement of each of the movable members toward preset positions is complete. The strobe unit 15 then emits light to produce an image.

Figure 12A:
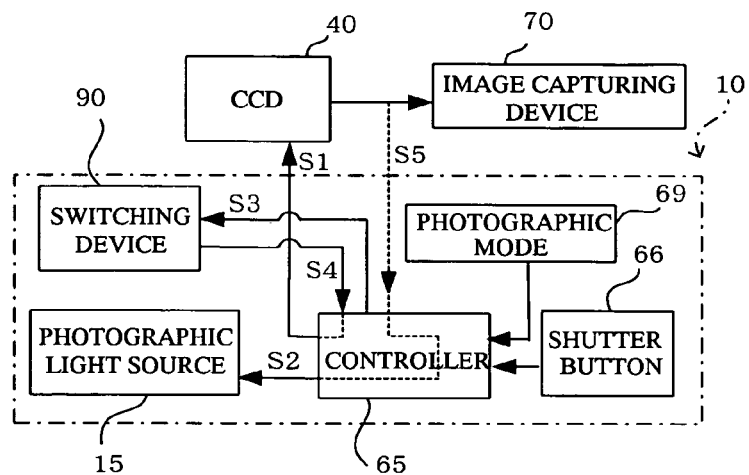
FIG. 12a is a block diagram showing still yet another example of a system for generating a trigger signal a preset number of times and capturing images by a single operation of a shutter button.
Figure 12B:
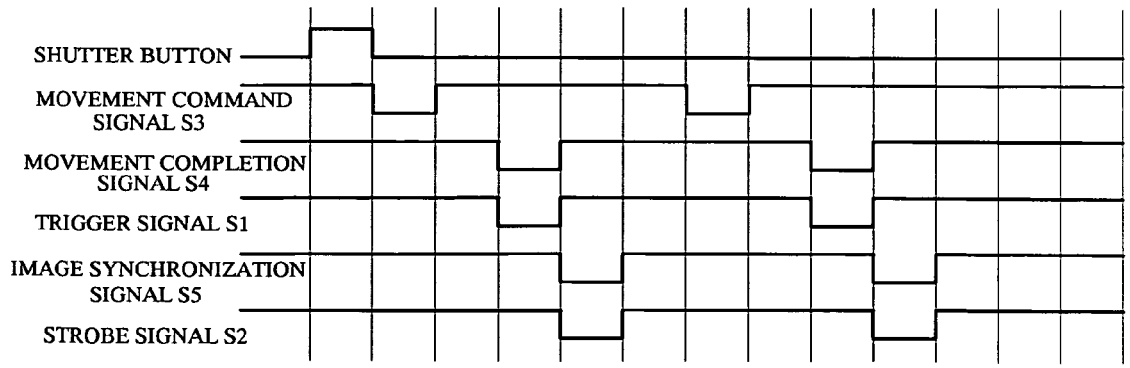
FIG. 12b is a timing diagram showing the timing at which the signals are generated.

In the example shown in FIGS. 12a and 12b, a movement command signal S3 for moving each of the movable members to preset positions is output by the controller 65 to the switching device 90 via the operation of the shutter button 66. The switching device 90 switches to the photographic stop, illumination stop, and black spot at positions suitable for photographing. The controller 65 receives a movement completion signal S4 from the switching device 90 and issues a trigger signal S1 to the CCD 40 synchronously with the movement completion signal S4. A strobe signal S2 is then generated by the controller 65 synchronously with an image synchronization signal S5 generated by the CCD 40. This causes the strobe unit 15 to emit light for photographing.

Only stereophotography is described in the examples shown in FIGS. 10, 11, and 12. However, when normal photographic mode is selected, a single photographic operation is performed by a single operation of the shutter button 66. In such instances, the timing of the operations is the same as the timing during the first photographic operation according to the stereo mode timing shown in FIGS. 10, 11, and 12. The difference is that the switching device 90 switches the photographic stop, illumination stop, and black spot so that they are suitable for normal photographic mode.

In the examples of FIGS. 7 through 12, a photographic mode may be selected in which normal photography is performed and stereo photography is then performed in succession so that three images are continuously formed. In such a mode, a single operation of the shutter causes three photographic operations to be performed in succession. In the first operation, the same photographic conditions are used as in normal photographic mode, while in the second and third operations, the same conditions are used as those when the first and second images are formed in stereo photographic mode.

When a trigger signal is emitted a plurality of times in the examples described above, the interval therebetween is harmonized in advance with a period allowing images to be created by the imaging device (CCD).

Once a trigger signal has been generated by the controller 65, signals are generated such as a trigger mask signal for keeping the same trigger signal from being generated for a set period of time, a strobe mask signal for keeping photographic operations such as the emission of the strobe light by a strobe signal from being performed multiple times, and the like. In addition, when the controller generates a strobe-enabling signal for enabling the input of the strobe signal from an external source, the period of time during which the strobe-enabling signal is generated differs depending on whether normal or stereo photographic mode has been selected. For example, the time for generating the strobe-enabling signal is set to less than one frame in normal mode and to greater than two frames in stereo mode. A fixed interval can also be provided so that the strobe-enabling signal can be generated a number of times harmonized to the number of times the strobe signal is generated.

Figure 13:
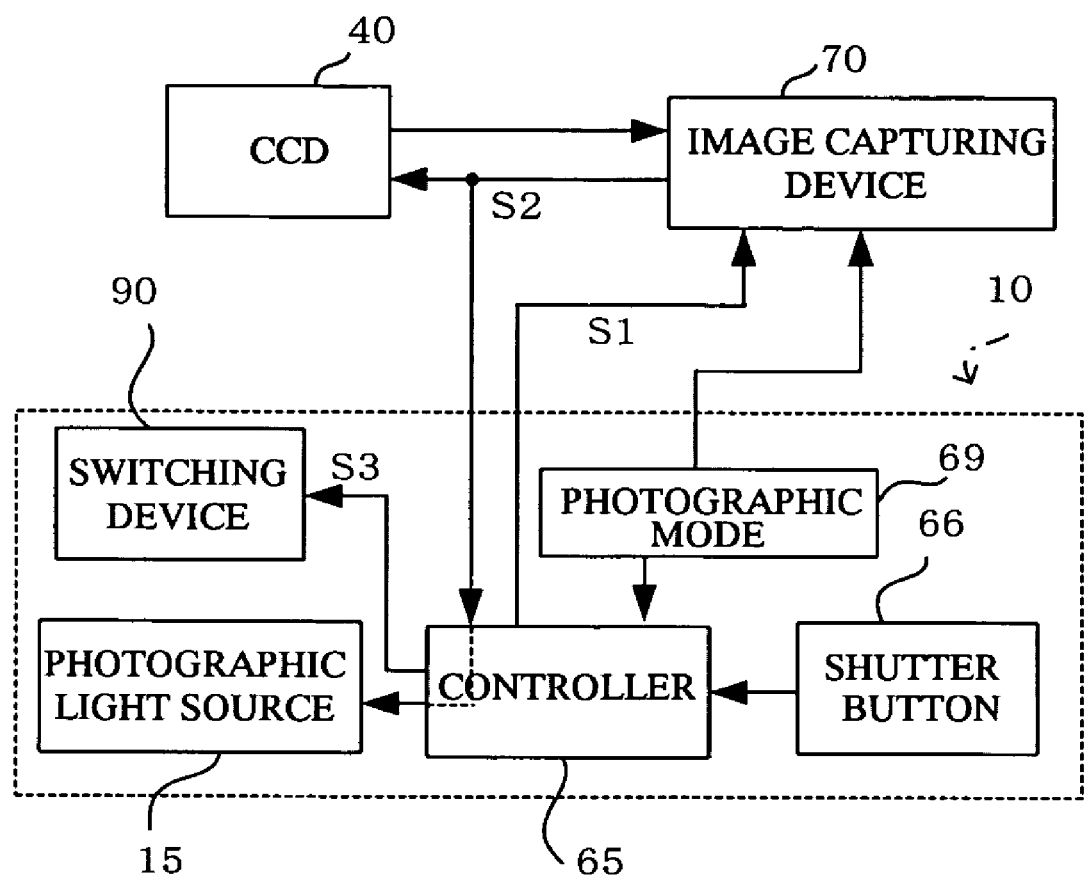
FIG. 13 is a block diagram showing an example of a system for generating a strobe signal a preset number of times and capturing images by a single operation of a shutter button.

In the embodiment as shown in FIG. 13, a strobe signal to the fundus camera is generated a designated number of times in accordance with the photographic mode by a single operation of the shutter button. The same numeric symbols are assigned to parts that are the same as in the embodiments as described above. The embodiment in FIG. 13 has the same configuration and functions as in FIG. 1 and has the same functions. Descriptions thereof will accordingly be omitted.

In the embodiment in FIG. 13, the image capturing device 70 receives a signal that indicates the mode selected by the photographic mode selecting means 69 and a trigger signal S1 generated by the controller 65 by the operation of the shutter button 66. A single push of the trigger button 66 causes the control computer 71 to output a strobe signal S2 once each to the controller 65 and the CCD 40 when normal photography has been selected, or output a strobe signal S2 multiple times (two times) each to the controller 65 and CCD 40 if stereo photography has been selected. If three-image serial photography is selected, a single push of the trigger button 66 will cause a strobe signal S2 to be output three times each to the controller 65 and the CCD 40.

Each time a strobe signal S2 is output, the strobe unit 15 is caused to emit light by a synchronization signal from the controller 65 or a synchronization signal from the image capturing device 70. In such instances, a movement command signal S3 from the controller 65 causes the switching device 90 to switch the positions of the photographic stop, illumination stop, and black spot to positions that are suitable for each photography, thus enabling the photography according to each photographic mode to be performed.

The examples shown in FIGS. 7 and 8 can be used to show the timing for generating the trigger signal S1, strobe signal S2, and movement command signal S3, while the example shown in FIG. 9 can be used to show the timing when the movement completion signal S4 is also used.

Also in the embodiment in FIG. 13, when the strobe signal is generated multiple times, the interval at which the strobe signals are generated is harmonized with a period at which images are produced by the imaging device (CCD).

Figure 14:
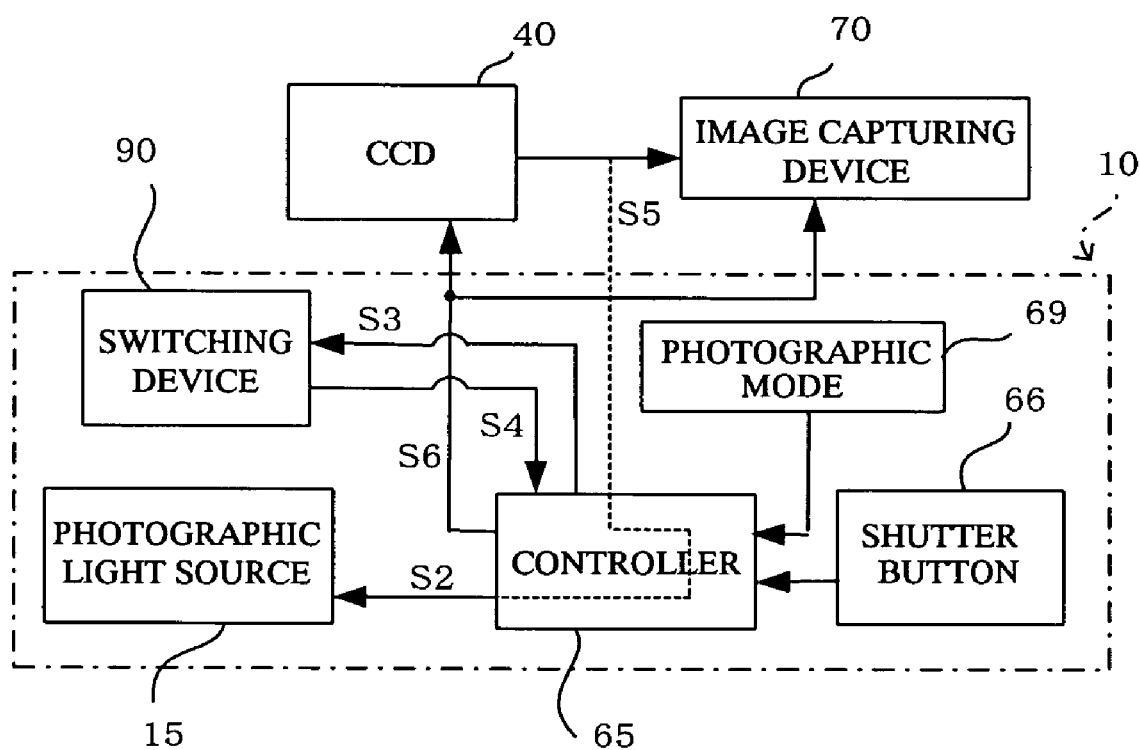
FIG. 14 is a block diagram showing another example of a system for generating a strobe signal a preset number of times and capturing images by a single operation of a shutter button.

In the embodiment shown in FIG. 14, a strobe signal is generated a number of times in accordance with the photographic mode by a single operation of the shutter, as in the embodiment in FIG. 13. The same numeric symbols are applied to parts that are the same as those in the embodiments that have already described. The embodiment in FIG. 14 has the same configuration and functions as in FIG. 1 and has the same functions. Descriptions thereof will accordingly be omitted.

In the embodiment in FIG. 14, when the shutter button 66 is operated, a mode switching signal S6 is input to the CCD 40 and image capturing device 70 in accordance with the mode selected by the photographic mode selection means 69. The mode is switched to still-image photography when normal photographic mode has been selected, and to moving-image photography when stereo photographic mode has been selected. In the embodiment in FIG. 14, an image synchronization signal S5 output from the CCD 40 is used as a strobe signal S2.

An instance in which stereo mode is selected by the photographic mode selection means 69 in this embodiment will be described with reference to the timing charts shown in FIGS. 15 and 16. Since stereo photographic mode has been selected, the mode switching signal S6 switches the CCD 40 and the image capturing device 70 to moving-image photography, and the image capturing device 70 continuously captures a moving image from the CCD 40.

Figure 15A:
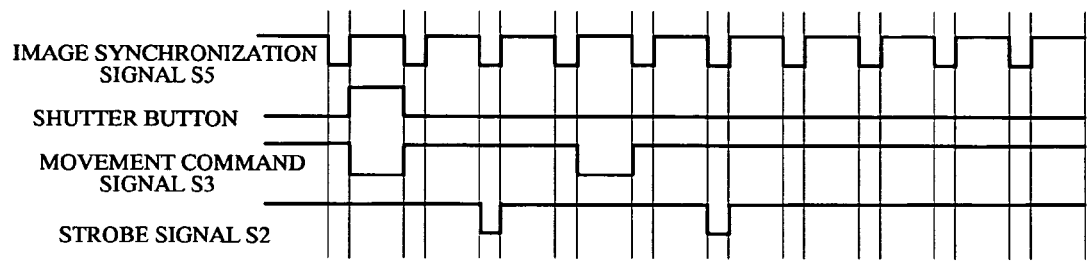
FIGS. 15a through 15c are timing diagrams showing points at which the signals are generated in the configuration of FIG. 14.

In the example shown in FIG. 15a, when the shutter button 66 is operated, a movement command signal S3 is output synchronously with the operation thereof. The switching device 90 accordingly moves the movable members (32, 19, 82) and switches to a photographic stop, illumination stop, and black spot that are suitable for producing one image having the parallax of a stereo image. A strobe signal S2 is then generated synchronously with a movement synchronization signal S5 generated after a set period of time, the strobe unit 15 emits light, and one image for stereoscopic viewing is obtained. Next, a second movement command signal S3 causes the switching device 90 to switch to a photographic stop, illumination stop, and black spot that are suitable for producing another image having the parallax of a stereo image. A second strobe signal S2 is generated synchronously with the subsequent movement synchronization signal S5 to thereby obtain the other image having the parallax of a stereo image.

Figure 15B:
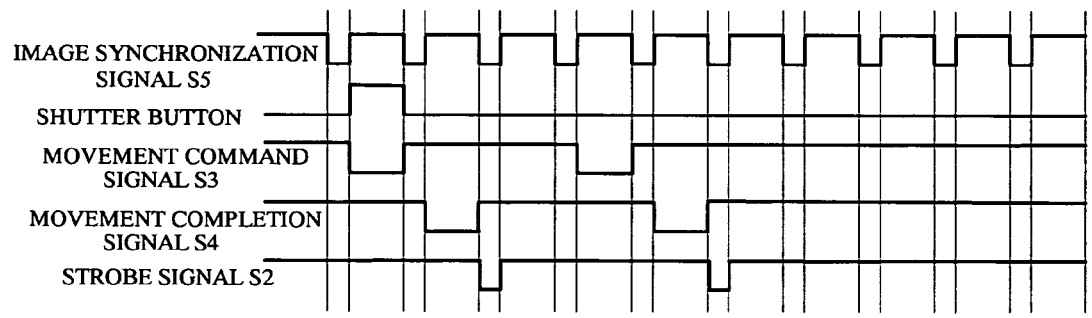
Figure 15C:
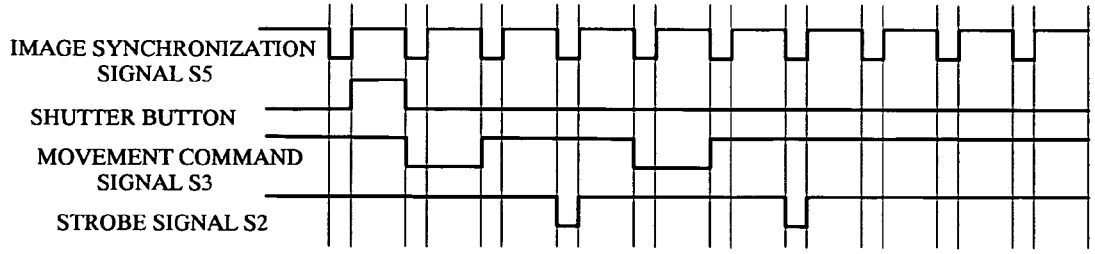

In the example shown in FIG. 15b, a strobe signal S2 is generated synchronously with an image synchronization signal S5 generated after the controller 65 receives a movement completion signal S4. In the example shown in FIG. 15c, a movement command signal S3 is generated synchronously with an image synchronization signal S5 generated after the shutter button 66 is operated, and a strobe signal S2 is generated after a certain period of time.

Figure 16A:
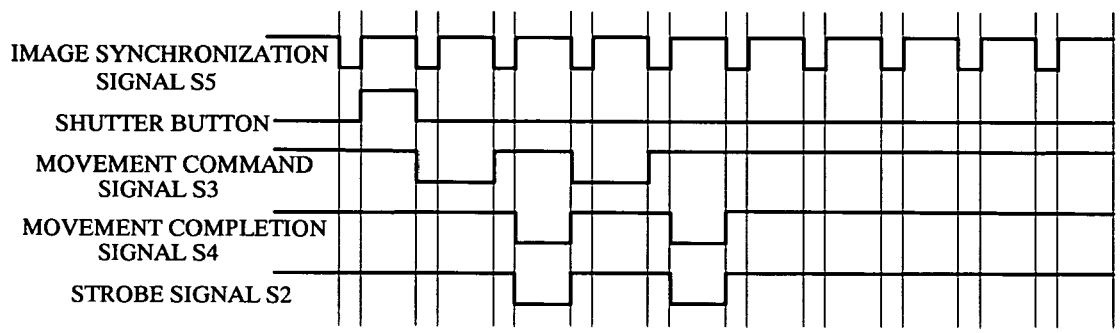
FIGS. 16a and 16b are timing diagrams showing points at which the signals are generated in the configuration of FIG. 14.
Figure 16B:
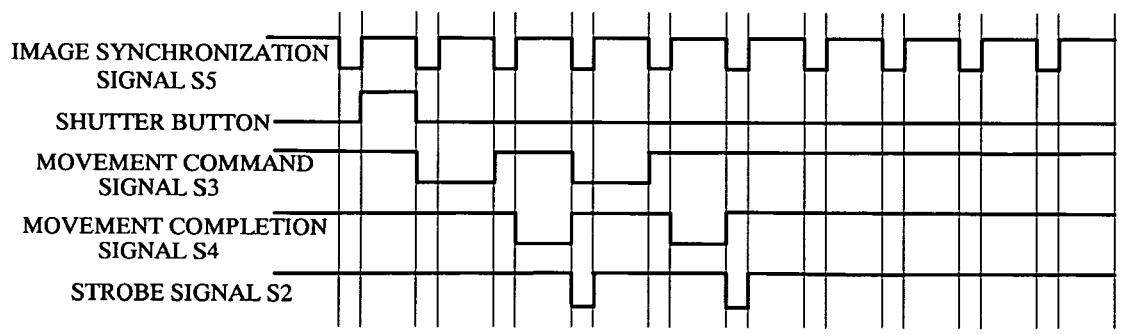

In the example shown in FIG. 16a, a movement command signal S3 is generated synchronously with an image synchronization signal S5 generated after the shutter button 66 is operated. A strobe signal S2 is then transmitted directly after the controller 65 receives a movement completion signal S4. In the example shown in FIG. 16b, a movement command signal S3 is generated synchronously with an image synchronization signal S5 generated after the shutter button 66 is operated, and a strobe signal S2 is generated synchronously with an image synchronization signal S5 generated after the controller 65 receives a movement completion signal S4.

In FIGS. 15b, 15c, 16a, and 16b, the second strobe signals S2 are each generated using the same timing as the first strobe signals.

In all of the examples, the image capturing device 70 continuously captures a moving image from the CCD 40, extracts an approximately fixed amount of frames of stroboscopically emitted light as still image data, stores the data in the memory 72, selects from the still image data only those images suitable for a fundus image, and saves the selected image data to the hard disk 73.

The examples described above pertain to the capturing of stereo images. However, when normal photographic mode is selected, the CCD 40 and image capturing device 70 are switched to still-image mode, a single strobe signal is generated by a single operation of the shutter button, the strobe emits light, and normal monocular photography is performed. The timings shown in FIGS. 15 and 16 are used for the timing associated with the generation of the strobe signal.

In all the embodiments already described, the captured images are stored in the memory 72 along with the type of mode used when the image was captured, the ID of the examined eye, the date the image was captured, the amount of light used (amount of light emitted by the strobe), the left/right eye determination, the position of the photographic stop, and other information. The images are then transmitted to the hard disk 73 at a preset timing, and saved thereon.

Additionally, in all the embodiments, when the images stored in the memory 72 or on the hard disk 73 are retrieved and displayed, the display method and display means (monitor) are changed in accordance with the photographic mode. For example, when a monocular fundus image captured using normal mode is displayed, the monitor 62 is selected automatically, and the fundus image is displayed as a still image on the monitor 62 along with information concerning the conditions under which the image was captured. When a right/left pair of images obtained using stereo mode is retrieved and the fundus is stereoscopically viewed, the images are shown on the stereo monitor 63 in the following manner. The left image accompanied by information concerning the left position is shown on the left side, and the right image accompanied by information concerning the right position is lined up with the right side of the left image and displayed along with the other information concerning the conditions under which the images were captured. On the other hand, when three images obtained using three-image serial mode are retrieved and displayed, the three images are repeatedly displayed one at a time on the monitor 62. A type of moving stereoscopic image can be displayed through this repeated display.

In all the embodiments, the present invention can be used in the same manner even when the imaging device (CCD) 40 and the image capturing device 70 are not provided to the exterior of the fundus camera unit 10, but are instead housed therein.

Additionally, in all the embodiments, light used to illuminate the object being imaged (strobe light) can be constantly emitted in a fixed amount during the period when multiple images are captured, as opposed to being emitted for each of a plurality of images to be captured. In such instances, a control signal used for the strobe need not be sent for each image captured. An advantage is accordingly presented in that the control circuit is simplified.

Figure 17A:
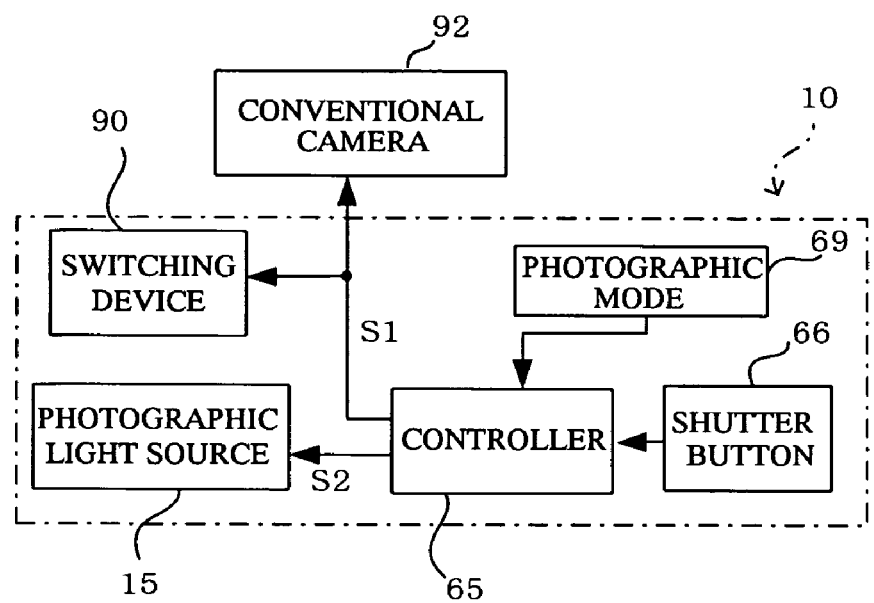
FIG. 17a is a block diagram of an imaging system in which a conventional camera is employed.

An embodiment is shown in FIG. 17a that does not involve an electronic image being obtained using a CCD as an imaging device, but instead involves a fundus being photographed on a film using a conventional camera 92 comprising a mechanical shutter.

Figure 17B:
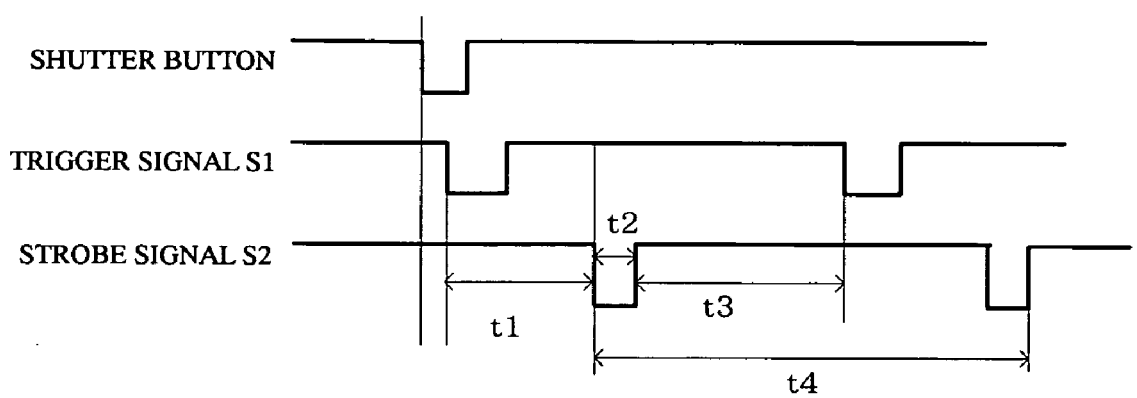
Figure 18A:
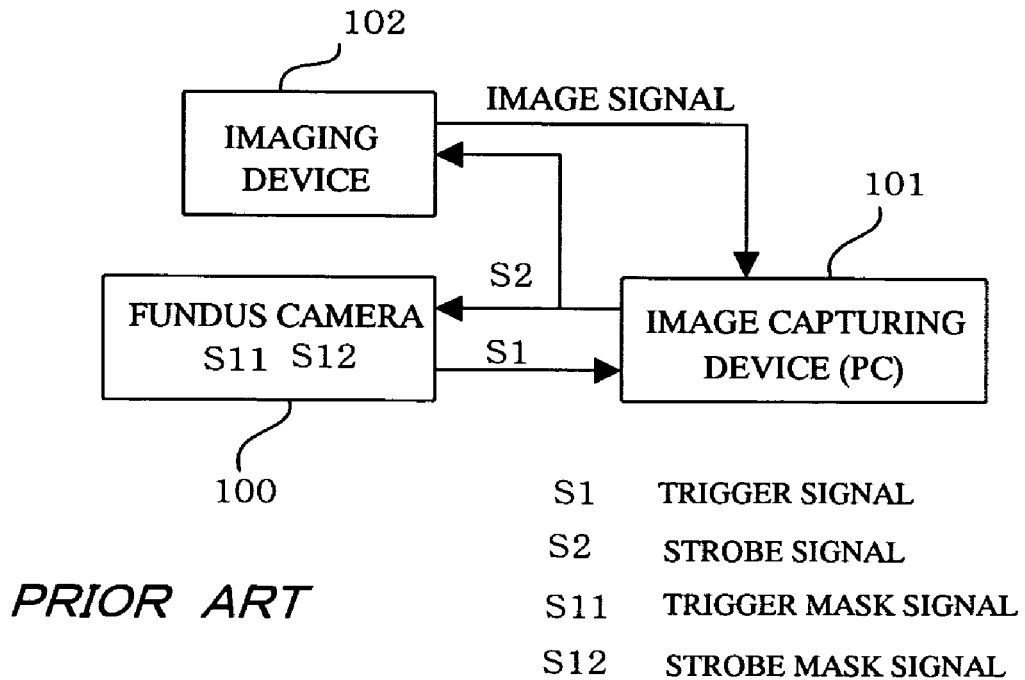
FIGS. 18a and 18b are block diagrams each showing a conventional imaging system.
Figure 18B:
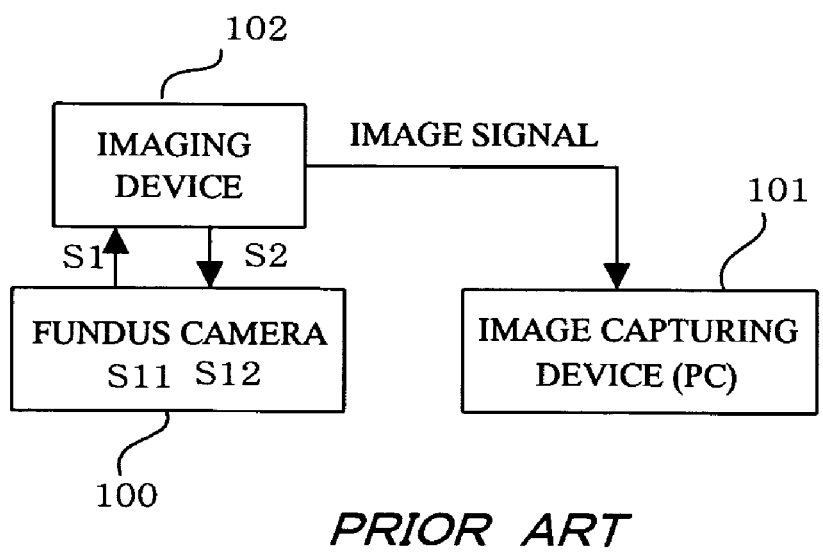

As shown in FIG. 17b, when the shutter button 66 is operated in this embodiment, a trigger signal S1 is transmitted from the controller 65 to the switching device 90 and a shutter mechanism of the conventional camera 92. The switching device 90 switches to the photographic stop, illumination stop, and black spot suitable for capturing images as designated by the photographic mode in the same manner as in the embodiments using CCD camera, and the shutter of the conventional camera 92 is opened. A strobe signal S2 is then output to the strobe unit 15 after a shutter opening time t1 has elapsed, and the strobe unit 15 is caused to emit light. The process ends at this point in normal mode. However, when stereo mode has been selected, a second trigger signal S1 is generated after an exposure time t2 and film winding time t3 have elapsed. The photographic stop and other components are then switched by the switching device 90, a second strobe signal S2 is generated when the mechanical shutter is opened, and photographing is performed for a second time. The interval t4 between two strobe signals are, for example, about 200 ms.

What is claimed is:

1. An imaging system for controlling a photographic operation in which a shutter button is operated to cause a photographic light source to momentarily emit light to photograph an object, the imaging system comprising:
   an objective lens having a photographic optical axis;
   a fixed stop having a first photographic stop provided at a central part thereof coaxial with the photographic optical axis of the objective lens and having second and third photographic stops disposed on respective optical path positions of a laterally divided photographic optical path;
   a movable stop unit configured to undergo movement relative to the fixed stop to selectively open an opening of one of the first, second and third photographic stops and configured to stop moving when the opening of one of the first, second and third photographic stops is selectively opened by the movable stop unit;
   means for generating a movement completion signal indicating that movement of the movable stop unit is stopped;
   selecting means for selecting between first and second photographic modes;
   control means for controlling the movable stop unit to move to a first position to open the opening of the first photographic stop when the first photographic mode is selected by the selecting means and for controlling the movable stop unit to move to second and third positions to open the openings of the second and third photographic stops, respectively, when the second photographic mode is selected by the selecting means; and
   imaging means for imaging the object;
   wherein when the first photographic mode is selected by the selecting means, a single operation of the shutter button causes a single photographic operation to be performed by moving the movable stop unit to the first position to open the opening of the first photographic stop;
   wherein when the second photographic mode is selected by the selecting means, a single operation of the shutter button causes two photographic operations to be successively performed by moving the movable stop unit to the second position to open the opening of the second photographic stop and by moving the movable stop unit to the third position to open the opening of the third photographic stop; and
   wherein when the shutter button is operated in the second photographic mode, a trigger signal for triggering the imaging means to image the object and a movement command signal for moving the movable stop unit to the second position to open the opening of the second photographic stop are generated and thereafter a strobe signal that causes the photographic light source to emit light is generated to photograph the object via the second photographic stop, followed by the subsequent generation of the trigger signal and the movement command signal for moving the movable stop unit to the third position to open the opening of the third photographic stop and generation of the strobe signal that causes the photographic light source to emit light to photograph the object via the third photographic stop, the strobe signal being generated synchronously with or after the generation of the movement completion signal.

2. An imaging system according to claim 1; wherein the movement command signal is generated synchronously with the trigger signal.

3. An imaging system according to claim 1; wherein the movement command signal is generated before the trigger signal.

4. An imaging system according to claim 1; wherein the movement command signal is generated after the trigger signal.

5. An imaging system according to claim 1; further comprising means for providing information concerning the selected photographic mode to an image captured when the object is photographed in the selected photographic mode.

6. An imaging system according to claim 1; further comprising means for providing information concerning the position of the movable stop unit to an image captured when the object is photographed in the selected photographic mode.

7. An imaging system according to claim 1; wherein the object photographed is a fundus of an eye.

8. An imaging system for controlling a photographic operation in which a shutter button is operated to cause a photographic light source to momentarily emit light to photograph an object, the imaging system comprising:
   an objective lens having a photographic optical axis;
   a fixed stop having a first photographic stop provided at a central part thereof coaxial with the photographic optical axis of the objective lens, and second and third photographic stops disposed on respective optical path positions of a laterally divided photographic optical path;
   a movable stop unit configured to undergo movement relative to the fixed stop to selectively open an opening of one of the first, second and third photographic stops and configured to stop moving when the opening of one of the first, second and third photographic stops is selectively opened by the movable stop unit;
   means for generating a movement completion signal indicating that movement of the movable stop unit is stopped;
   selecting means for selecting between first and second photographic modes;
   imaging means for imaging the object and generating image synchronization signals; and
   control means for: (a) controlling the photographic operation such that, when the first photographic mode is selected by the selecting means, a single operation of the shutter button causes the photographic light source to emit light for still image photography and, when the second photographic mode is selected by the selecting means, a single operation of the shutter button causes the object to be photographed as a moving image for a predetermined period of time; (b) controlling the photographic operation such that when the second photographic mode is selected, a single operation of the shutter button causes the control means to generate two strobe signals synchronously with the image synchronization signals to cause the photographic light source to emit light a plurality of times during the predetermined period of time, the image synchronization signals being generated by the imaging means after the movement completion signal is received by the control means; and (c) controlling the photographic operation so that the photographic light source is caused to emit light with one of the two strobe signals to photograph the object via the first photographic stop and to emit light with the other of the two strobe signals to photograph the object via one of the second and third photographic stops.

9. An imaging system according to claim 8; further comprising means for extracting an image from the moving image and storing the image as a still image when the photographic light source is caused to emit light.

10. An imaging system according to claim 8; further comprising means for providing information concerning the selected photographic mode to an image captured when the object is photographed in the selected photographic mode.

11. An imaging system according to claim 8; wherein the object photographed is a fundus of an eye.

12. An imaging system for controlling a photographic operation to photograph an object to be examined, the imaging system comprising:
   an objective lens having a photographic optical axis;
   a fixed stop having a first photographic stop provided at a central part thereof coaxial with the photographic optical axis of the objective lens, and second and third photographic stops disposed on respective optical path positions of a laterally divided photographic optical path;
   a movable stop unit configured to undergo movement relative to the fixed stop to selectively open an opening of one of the first, second and third photographic stops and configured to stop moving when the opening of one of the first, second and third photographic stops is selectively opened by the movable stop unit;
   means for generating a movement completion signal indicating that movement of the movable stop unit is stopped;
   a photographic mode selector that selects between first and second a photographic modes;
   an imaging device that images the object to be examined;
   a photographic light source that emits light; and
   a control unit that controls the movable stop unit to move to a first position to open the opening of the first photographic stop when the first photographic mode is selected by the photographic mode selector and that controls the movable stop unit to move to second and third positions to open the openings of the second and third photographic stops, respectively, when the second photographic mode is selected by the photographic mode selector means;
   wherein when the first photographic mode is selected by the photographic mode selector, a single photographic operation is performed by movement of the movable stop unit to the first position to open the opening of the first photographic stop;
   wherein when the second photographic mode is selected by the photographic mode selector, two photographic operations are successively performed by movement of the movable stop unit to the second position to open the opening of the second photographic stop and by movement of the movable stop unit to the third position to open the opening of the third photographic stop; and
   wherein in the second photographic mode, a trigger signal that triggers the imaging device to image the object and a movement command signal that moves the movable stop unit to the second position to open the opening of the second photographic stop are generated and thereafter a strobe signal that causes the photographic light source to emit light is generated to photograph the object to be examined via the second photographic stop, followed by the subsequent generation of the trigger signal and the movement command signal that moves the movable stop unit to the third position to open the opening of the third photographic stop and by generation of the strobe signal that causes the photographic light source to emit light to photograph the object to be examined via the third photographic stop, the strobe signal being generated synchronously with or after the generation of the movement completion signal.

13. An imaging system according to claim 12; wherein the object to be examined comprises a fundus of a patient's eye.

14. An imaging system according to claim 12; further comprising a shutter button operable to cause the photographic light source to emit light; and wherein in the first photographic mode, the single photographic operation is caused by a single operation of the shutter button; and wherein in the second photographic mode, the two photographic operation is caused by a single operation of the shutter button.

15. An imaging system according to claim 12; wherein the movement command signal is generated synchronously with the trigger signal.

16. An imaging system according to claim 12; wherein the movement command signal is generated before the trigger signal.

* * * * *